(12) United States Patent
Yuhasz et al.

(10) Patent No.: US 6,273,918 B1
(45) Date of Patent: Aug. 14, 2001

(54) MAGNETIC DETACHMENT SYSTEM FOR PROSTHETICS

(76) Inventors: Jason R. Yuhasz, 25 Capital Ave., Oaklyn, NJ (US) 08107; John Paolone, Jr., 3 Kingsley Rd., Easthampton, NJ (US) 08060

(*) Notice: Subject to any disclaimer, the term of this patent is extended or adjusted under 35 U.S.C. 154(b) by 0 days.

(21) Appl. No.: 09/383,503

(22) Filed: Aug. 26, 1999

(51) Int. Cl.⁷ ...................................................... A61F 2/80
(52) U.S. Cl. .................................................. 623/33; 623/36
(58) Field of Search .............................. 623/33, 32, 36, 623/27; 223/11, 12, 13

(56) References Cited

U.S. PATENT DOCUMENTS

| | | | |
|---|---|---|---|
| 4,743,264 | 5/1988 | Sherva-Parker | 623/33 |
| 5,139,523 | 8/1992 | Paton et al. | 623/37 |
| 5,226,918 | 7/1993 | Silagy et al. | 623/32 |
| 5,507,835 | 4/1996 | Jore | 623/36 |
| 5,507,837 | 4/1996 | Laghi | 623/38 |

*Primary Examiner*—David H. Willse
*Assistant Examiner*—Alvin Stewart
(74) *Attorney, Agent, or Firm*—Henderson & Sturm LLP

(57) ABSTRACT

A magnetic detachment system 10 for prosthetics which includes a prosthetic sleeve member 20 having a dosed end 22 provided with a first magnetic member 23, a prosthesis unit 12 including a prosthetic socket member 30 having a closed end 32 provided with a second magnetic member 33, and a detachment unit 13 including a detachment member 60 having a generally flat head element 61 which can be interposed between the first and second magnetic members 23, 33 to separate the sleeve member 20 from the socket member 30.

11 Claims, 2 Drawing Sheets

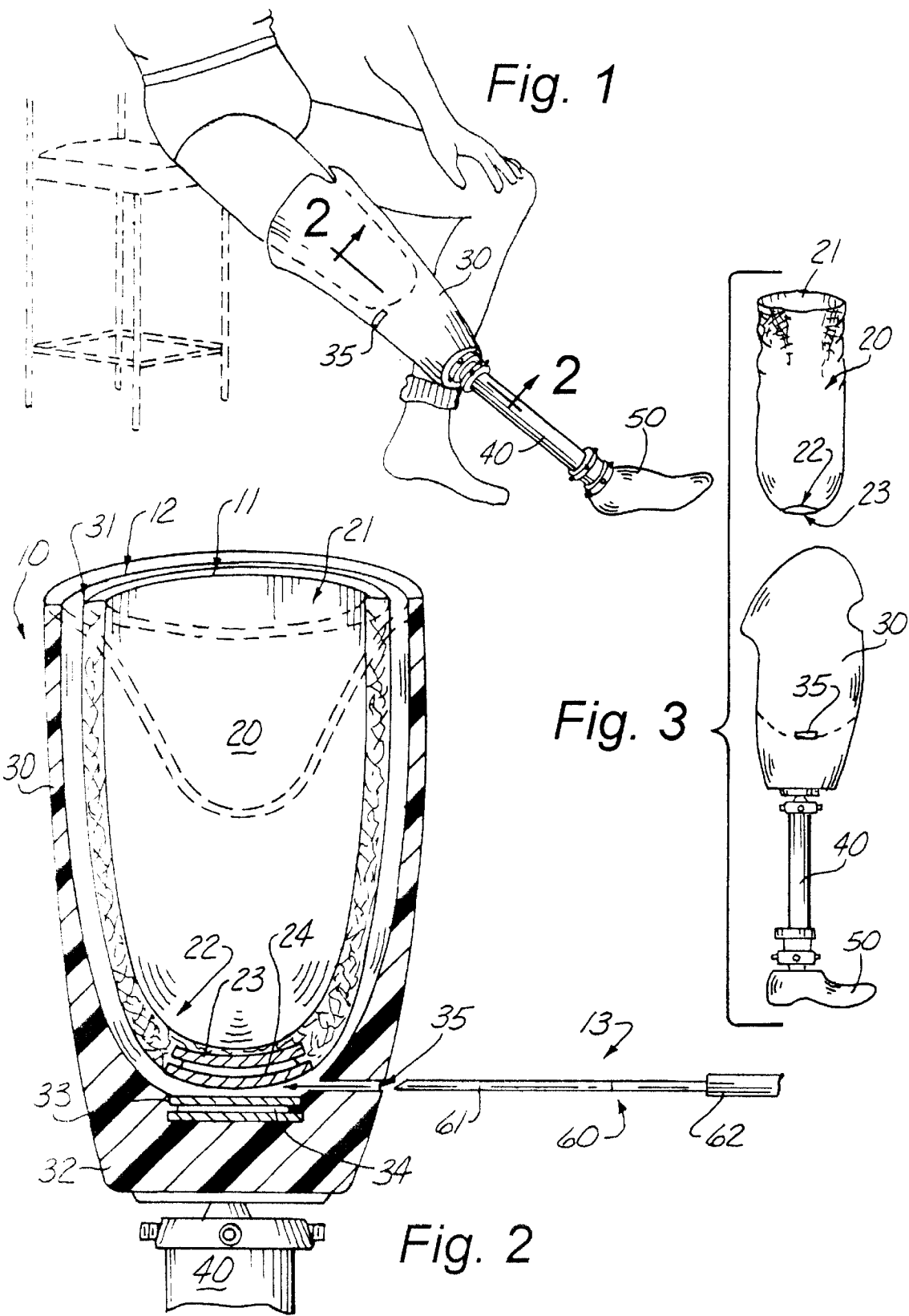

MAGNETIC DETACHMENT SYSTEM FOR PROSTHETICS

BACKGROUND OF THE INVENTION

1. Field of the Invention

The present invention relates to the field of prosthetic attachment systems in general, and in particular to a prosthetic detachment system that employs a means for interrupting the magnetic attraction between a magnetized prosthesis and prosthesis sock.

2. Description of Related Art

As can be seen by reference to the following U.S. Pat. Nos. 4,743,264; 5,139,523; 5,226,918; 5,507,835; and 5,507,837, the prior art is replete with myriad and diverse prosthesis attachment systems including at least one such system that relies upon magnetic attraction.

While all of the aforementioned prior art constructions are more than adequate for the basic purpose and function for which they have been specifically designed, they are uniformly deficient with respect to their failure to provide a simple, efficient, and practical method for effecting the releasable engagement between a magnetically engaged prosthesis and prosthetic sock.

As most amputees are all too well aware, one of the main problems with wearing a prosthesis involves the engagement and/or disengagement of the prosthetic sock with the prosthesis.

This is particularly true in a magnetic attachment system wherein the relative strength of the magnets employed to ensure a secure connection between the components also creates a proportionate problem in separating the components when desired.

As a consequence of the foregoing situation, there has existed a longstanding need for a new and improved method of disengaging a prosthetic sock having a magnetic member from a prosthesis sleeve that is likewise equipped with another magnetic member, and the provision of such a construction is a stated objective of the present invention.

BRIEF SUMMARY OF THE INVENTION

Briefly stated, the magnetic detachment system for prosthetics comprises in general, a detachment tool that can be interposed between the magnetically attractive members that are embedded in both a prosthetic sleeve and the socket portion of the prosthesis to disrupt the magnetic attraction between the magnetically attractive members to permit the prosthetic sleeve to be easily removed from the magnetic socket.

As will be explained in greater detail further on in the specification, the socket portion of the prosthesis is provided with an elongated horizontally disposed slot which extends through at least one side of the socket and is generally aligned in a tangential fashion with the top surface of the magnetic member that is disposed within the socket portion such that a detachment tool can be interposed between the magnetic members in both the prosthetic socket and the prosthetic sleeve to disengage the magnetic members.

In one version of the preferred embodiment, the detachment tool has a magnetic head wherein the magnetic poles are inserted in a repelling fashion relative to the magnetic poles of the respective magnetic members in both the prosthetic sleeve and socket. In the other version of the preferred embodiment, the head of the detachment tool is magnetically inert and relies on a forcible manual separation of the magnetic members to reduce the force of the magnetic attraction between the two magnetic members.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of a magnetic prosthetic system employing the teachings of this invention;

FIG. 2 is a cross sectional view showing all of the major components of the system;

FIG. 3 is an exploded perspective view of the main components of the prosthesis;

DETAILED DESCRIPTION OF THE INVENTION

Figure 4:
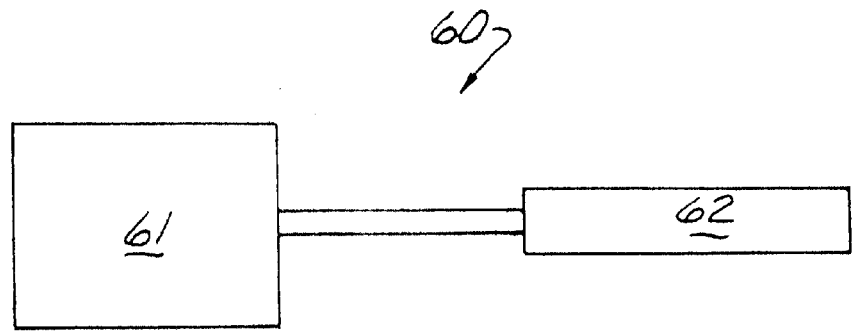
FIG. 4 is a top plan view of the detachment tool.

As can be seen by reference to the drawings, and in particular to FIG. 2, the magnetic detachment system for prosthetics that forms the basis of the present invention is designated generally by the reference number 10. The main components of the system 10 comprise a prosthetic sleeve unit 11, a prosthesis unit 12, and a detachment unit 13. These units will now be described in seriatim fashion.

As shown in FIGS. 1 through 3, the prosthetic sleeve unit 11 comprises a silicone impregnated sleeve liner member 20 having an open end 21 dimensioned to receive a limb stump and a closed curved lower end 22 provided with an upper curved convex magnetic member 23 having a lateral groove 24 to facilitate the engagement of the curved magnetic member 23 in the bottom 22 of the sleeve liner member 20.

In addition, the prosthesis unit 12 comprises a generally rigid prosthetic socket member 30 mounted on a pylon member 40 whose lower end is provided with a prosthetic limb extremity 50 such as an artificial hand or foot.

The prosthetic socket member 30 has an open end 31 dimensioned to receive the sleeve liner member 20 and a closed curved lower end 32 provided with a generally flat rectangular magnetic member 33 having a lateral groove 34 to facilitate the engagement of the generally flat magnetic member 33 which extends into the upper portion of the curved lower end 32 of the socket member 30.

Still referring to FIGS. 1 through 3, it can be seen that at least one side of the prosthetic socket member 30 is provided with an elongated generally horizontally disposed slot 35 which intersects the interior of the socket member 30 in a tangential fashion with the top surface of the generally flat rectangular magnetic member 33 and dimensioned to receive the detachment unit 13 for reasons that will be explained presently.

Figure 5:
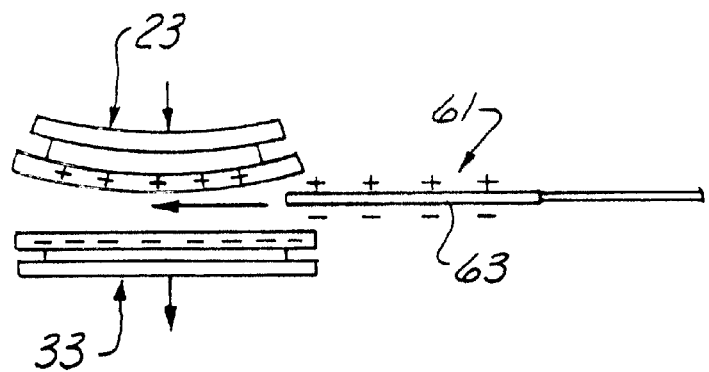
FIG. 5 is an enlarged cross sectional view of the magnetic version of the detachment tool employed in this system.
Figure 6:
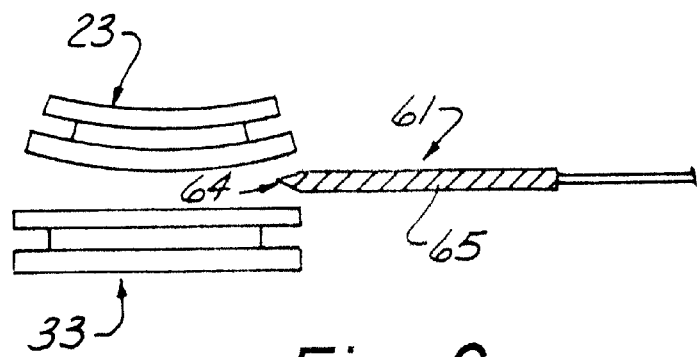
FIG. 6 is an enlarged cross sectional view of the magnetically inert version of the detachment tool employed in the system.

Turning now to FIGS. 4 through 6, it can be seen that the detachment unit 13 comprises a detachment member 60 having an enlarged generally flat head element 61 formed on one end and a handle element 62 formed on the other end. The head element 61 is dimensioned to be slidably received in the slot 35 in the prosthetic socket member 30 to disengage the upper curved magnetic member 23 from the lower generally flat magnetic member 33.

In the first version of the preferred embodiment illustrated in FIG. 5, the generally flat head element 61 is fabricated from a magnetic material 63. The magnetic poles represented by (+) and (−) signs are disposed in a repelling fashion relative to the corresponding poles of the upper 23 and lower 33 magnetic members such that when the head element 61 is inserted into the slot 35, the repelling magnetic forces will force the upper 23 and lower 33 magnetic members apart in a well recognized fashion.

Turning now to FIG. 6, it can be seen that in the second version of the preferred embodiment, the head element 61 is provided with a pointed leading edge 64 and fabricated from a magnetically inert material 65 such as hard plastic, or the like. The head element 61 relies upon a manual levering separation force to physically disengage the upper magnetic member 23 from the lower magnetic member 33 and the interposing movement of the magnetically inert head element 61 between the magnetic members 23, 33 interrupts the magnetic field between the two magnetic members 23, 33.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

We claim:

1. In a magnetic prosthesis system comprising a prosthetic sleeve member having a closed end provided with a first generally curved magnetic member and a prosthesis including a prosthetic socket member having an open end dimensioned to receive said prosthetic sleeve member and further having a closed end provided with a second generally flat magnetic member, an improvement comprising:

a detachment unit including a detachment member associated with said prosthetic socket member and provided with a head element that is adapted to be interposed between said first and second magnetic members for the purpose of separating the prosthetic sleeve member from the prosthetic socket member.

2. The improvement as in claim 1 wherein the head element has a generally flat configuration.

3. The improvement as in claim 2 wherein the head element is fabricated from a magnetic material.

4. The improvement as in claim 2 wherein the had element is provided with a leading edge which is pointed.

5. The improvement as in claim 4 wherein said head element is fabricated from a magnetically inert material.

6. The improvement as in claim 1 wherein at least one side of said prosthetic socket member is provided with an elongated slot dimensioned to receive the head element of the detachment member.

7. The improvement as in claim 6 wherein said slot is tangentially aligned with the top of said second magnetic member.

8. The improvement as in claim 7 wherein the head element has a generally flat configuration.

9. The improvement as in claim 8 wherein the head element is fabricated from a magnetic material.

10. The improvement as in claim 7 wherein the head element is provided with a leading edge which is pointed.

11. The improvement as in claim 10 wherein said head element is fabricated from a magnetically inert material.

\* \* \* \* \*